United States Patent
Yahata et al.

(10) Patent No.: US 10,694,812 B2
(45) Date of Patent: Jun. 30, 2020

(54) SHOE SOLE STRUCTURE AND SHOE USING SAME

(71) Applicant: Mizuno Corporation, Osaka (JP)

(72) Inventors: Kentaro Yahata, Osaka (JP); Takao Oda, Osaka (JP); Daisuke Kogawa, Osaka (JP)

(73) Assignee: Mizuno Corporation, Osaka (JP)

( * ) Notice: Subject to any disclaimer, the term of this patent is extended or adjusted under 35 U.S.C. 154(b) by 0 days.

(21) Appl. No.: 16/088,903

(22) PCT Filed: Feb. 23, 2017

(86) PCT No.: PCT/JP2017/006758
§ 371 (c)(1),
(2) Date: Sep. 27, 2018

(87) PCT Pub. No.: WO2017/169352
PCT Pub. Date: Oct. 5, 2017

(65) Prior Publication Data
US 2019/0116928 A1 Apr. 25, 2019

(30) Foreign Application Priority Data

Mar. 30, 2016 (JP) ................................ 2016-068979

(51) Int. Cl.
*A43B 13/18* (2006.01)
*A43B 13/14* (2006.01)
(Continued)

(52) U.S. Cl.
CPC ............ *A43B 13/186* (2013.01); *A43B 13/04* (2013.01); *A43B 13/12* (2013.01); *A43B 13/125* (2013.01);
(Continued)

(58) Field of Classification Search
CPC ..... A43B 13/186; A43B 13/12; A43B 13/125; A43B 13/188
(Continued)

(56) References Cited

U.S. PATENT DOCUMENTS

| 3,738,373 A | * | 6/1973 | Glancy | .................. A43B 21/26 36/144 |
| 4,364,189 A | * | 12/1982 | Bates | ....................... A43B 5/06 36/129 |

(Continued)

FOREIGN PATENT DOCUMENTS

| JP | 8205904 A | 8/1996 |
| JP | 970302 A | 3/1997 |

(Continued)

OTHER PUBLICATIONS

International Search Report and Written Opinion issued in counterpart International Application No. PCT/JP2017/006758 dated May 9, 2017.

*Primary Examiner* — Ted Kavanaugh
(74) *Attorney, Agent, or Firm* — Troutman Sanders LLP; James E. Schutz; Micah B. Hensley

(57) ABSTRACT

A sole structure is configured such that in a state where a ground surface of an outsole is in contact with the ground surface, when a planta support surface of a deformable part receives a load of a human body, the deformable part is flexurally deformed downward while being supported on a fixed end functioning as a supporting point, thereby allowing the planta support surface to be inclined downward such that a free end of the deformable part moves downward.

8 Claims, 17 Drawing Sheets

(51) Int. Cl.
*A61F 5/14* (2006.01)
*A43B 13/12* (2006.01)
*A43B 13/04* (2006.01)
*B32B 3/10* (2006.01)
*B32B 3/26* (2006.01)
*B32B 5/18* (2006.01)
*B32B 25/04* (2006.01)
*B32B 25/08* (2006.01)
*B32B 25/14* (2006.01)

(52) U.S. Cl.
CPC ............ *A43B 13/14* (2013.01); *A43B 13/188* (2013.01); *A61F 5/14* (2013.01); *B32B 3/10* (2013.01); *B32B 3/263* (2013.01); *B32B 5/18* (2013.01); *B32B 25/045* (2013.01); *B32B 25/08* (2013.01); *B32B 25/14* (2013.01); *B32B 2437/02* (2013.01)

(58) Field of Classification Search
USPC .......................................... 36/143, 144, 127
See application file for complete search history.

(56) References Cited

U.S. PATENT DOCUMENTS

| | | | | |
|---|---|---|---|---|
| 4,685,227 A * | 8/1987 | Simmons | ............... | A43B 17/02 36/127 |
| 4,864,739 A * | 9/1989 | Maestri | .................. | A43B 7/142 36/43 |
| 4,882,856 A * | 11/1989 | Glancy | .................. | A43B 21/32 36/43 |
| 4,890,397 A * | 1/1990 | Harada | ................ | A43B 13/187 36/114 |
| 5,561,919 A * | 10/1996 | Gill | .......................... | A43B 3/12 36/11.5 |
| 2011/0167674 A1* | 7/2011 | Langer | .................. | A43B 7/144 36/82 |

FOREIGN PATENT DOCUMENTS

| | | |
|---|---|---|
| JP | 2002153302 A | 5/2002 |
| JP | 2005224335 A | 8/2005 |
| JP | 2015208398 A | 11/2015 |

* cited by examiner

SHOE SOLE STRUCTURE AND SHOE USING SAME

This application is a U.S. National Stage of International Patent Application No. PCT/JP2017/006758, filed 23 Feb. 2017, which claims the benefit of Japanese Application No. JP2016-068979, filed 30 Mar. 2016. The entire contents of which are hereby incorporated in their entireties by reference herein.

TECHNICAL FIELD

The present invention relates to a shoe sole structure and a shoe using such a shoe sole structure. More specifically, the present invention relates to a shoe sole structure usable for treatment of knee osteoarthritis and a shoe using such a shoe sole structure.

BACKGROUND ART

Knee osteoarthritis is arthritis of a knee joint caused by wear of the cartilage of the knee joint due to various causes such as muscle weakness, aging, obesity. The knee osteoarthritis is a disorder that causes pain and swelling of the knee when the patient moves his/her legs (knees), for example, during walking. Generally, it is said that many Japanese suffer from knee osteoarthritis of a varus type (so-called bow legs), while many Europeans and Americans suffer from knee osteoarthritis of a valgus type (so-called knock knees). Treatment for the knee osteoarthritis is roughly classified into two types, i.e., conservative treatment and surgical treatment. The conservative treatment includes rehabilitation, orthotic therapy, physical therapy, and pharmacotherapy. Shoes for the orthotic therapy, which is an option of the conservative treatment, have been known from, for example, Patent Documents 1 and 2.

Patent Document 1 discloses shoes including an insole with an inclined hindfoot area formed on the back side of the insole. The inclined hindfoot area is located in a range between the foot outer side in an area corresponding to the hindfoot and a straight line connecting a point which is adjacent to the rear end of an area corresponding to the midfoot and adjacent to the foot inner side to a point which is adjacent to the rear end of the area corresponding to the hindfoot and adjacent to the foot inner side. The height of the inclined hindfoot area gradually increases in the direction from the straight line to the foot outer side, so that a surface located on the foot outer side is at a height higher by about 30% than a surface located on the foot inner side.

Patent Document 2 discloses a shoe including a sole (e.g., an insole). An area of the sole, which corresponds to a region, of a foot of a wearer, from the calcaneus to the vicinity of a front edge portion of the cuboid bone, gradually increases in thickness from the longitudinal center line to an outer edge of the sole. Another area of the sole, which corresponds to a region, of the wearer's foot, from the vicinity of the front edge portion of the cuboid bone to the vicinity of a front edge portion of the metatarsals, gradually increases in thickness from the longitudinal center line toward an inner edge of the sole.

CITATION LIST

Patent Documents

Patent Document 1: Japanese Unexamined Patent Publication No. 2015-208398
Patent Document 2: Japanese Patent No. 3140932

SUMMARY OF THE INVENTION

Technical Problem

The insole of Patent Document 1 and the insole of Patent Document 2 are both foot plates for use in the orthotic therapy that is one option of treatment for knee osteoarthritis. Both insoles are intended to correct the deformation in the knees of bow legs, and to diffuse and reduce a load unevenly applied to the inner side of each knee, by attaching the inclined surfaces having a slight inclination to the patient's plantar surfaces (so-called wedge therapy).

However, with these foot plates, the plantar surfaces of a patient wearing the shoes are in contact with the inclined surfaces of the shoe soles not only when the patient is moving his/her legs (knees), such as during walking, but also when the patient stands still (when the patient is not moving). That is, the foot plates of Patent Documents 1 and 2 will make a patient who suffers from knee osteoarthritis feel his/her plantar surfaces inclined at all time, in addition to when the patient is moving his/her knees during walking. Thus, the foot plates of Patent Documents 1 and 2 may have a side effect: the patient can adversely develop a habit of walking and standing with his/her plantar surfaces constantly inclined.

In view of the above background, it is therefore an object of the present invention to alleviate symptoms, such as pain and swelling of a knee joint, which are particularly liable to occur when a patient is moving (e.g., walking), while not allowing the patient to feel his/her plantar surfaces inclined except when the patient is moving so as to keep the patient from developing a habit of walking and standing with his/her plantar surfaces constantly inclined.

Solution to the Problem

To achieve the above object, a first aspect of the present invention is directed to a shoe sole structure including an outsole having a ground surface configured to contact with a ground surface, a midsole made from an elastic material and stacked on an upper portion of the outsole, and a deformable area provided in a medial side portion or a lateral side portion. The shoe sole structure includes at least one base part provided in a portion of the outsole, or a portion of the outsole and a lower portion of the midsole, the portions being located in the deformable area; and at least one deformable part provided in an upper portion of the midsole, the upper portion being located in the deformable area, the at least one deformable part corresponding to the at least one base part in a vertical direction, having a lower surface which faces an upper surface of the at least one base part with a gap interposed between the lower and upper surfaces, including, on an upper surface thereof, a planta support surface which is configured to support a planta of a human body, and being flexurally deformable while being supported on a fixed end on a base end side adjacent to a center in a shoe width direction such that a free end adjacent to an end in the shoe width direction moves downward to come close to the at least one base part. In a state where the ground surface of the outsole is in contact with the ground surface, when the planta support surface on the upper surface of the at least one deformable part receives a load of the human body caused by walking, the at least one deformable part is flexurally deformed downward while being supported on the fixed end functioning as a supporting point, thereby allowing the planta support surface to be inclined downward such that the free end of the deformable part moves downward.

According to the first aspect, for example, in a state where a patient wearing the shoes stands still (a non-moving state), a load caused by walking is not applied to the planta support surface of the deformable part. Thus, the deformable part is not deformed, and the planta support surface consequently remains substantially flat while the free end does not move downward. On the other hand, when the patient wearing the shoes steps forward with his/her foot and his/her shoe contacts with the ground surface during a movement such as walking, the planta support surface on the upper surface of the deformable part receives the load of the patient's body while the ground surface of the outsole is in contact with the ground surface. Due to the action of the load caused by waulking, the deformable part is flexurally deformed downward while being supported on the fixed end functioning as the supporting point, and consequently, the planta support surface is inclined downward such that the free end of the deformable part moves downward. As can be seen, the entire foot is inclined to one of the medial side or the lateral side of the shoe at the time when the patient steps on the ground during walking. This contributes to a decrease in a force applied to inside or outside portion of the patient's knee joint in a concentrated manner. Thus, the shoe sole structure of the first aspect can alleviate symptoms of a patient suffering from knee osteoarthritis, such as pain and swelling of a knee joint, which are liable to occur during a movement such as walking, while not allowing the patient to feel his/her plantar surfaces inclined except when the patient is moving, and keeping the patient from developing a habit of walking and standing with his/her plantar surfaces constantly inclined.

A second aspect of the present invention is an embodiment of the first aspect. In the second aspect, the gap between the lower surface of the deformable part and the upper surface of the base part narrows in a direction from a distal end side to the base end side of the deformable part.

According to the second aspect, the gap between the lower surface of the deformable part and the upper surface of the base part narrows in a direction from a distal end side to a base end side of the deformable part. Thus, the free end of the deformable part can make a relatively large movement toward the base part. As a result, the planta support surface is easily inclined downward such that the free end of the deformable part moves downward.

A third aspect of the present invention is an embodiment of the first or second aspect. In the third aspect, a buffer part made from a soft elastic material which is softer than the midsole is embedded in the midsole between the deformable part and the base part.

According to the third aspect, the buffer part is embedded in the midsole between the deformable part and the base part. This configuration can substantially prevent abrupt flexural deformation which may occur in the deformable part when the load of a human body is applied to the planta support surface of the deformable part, and can impart appropriate cushioning properties to the deformable part.

A fourth aspect of the present invention is an embodiment of any one of the first to third aspects. In the fourth aspect, the planta support surface of the deformable part is configured to support a region, of the planta, extending from a rear portion of a forefoot located rearward of metatarsophalangeal joints to a hindfoot.

The configuration of the fourth aspect makes it possible to efficiently incline the planta support surface of the deformable part, mainly in a region extending from a rear portion of a forefoot located rearward of the metatarsophalangeal joints to a hindfoot, toward the medial side, wherein an area of the shoe sole corresponding to this region mainly contacts with the ground surface during walking.

A fifth aspect of the present invention is an embodiment of any one of the first to fourth aspects. In the fifth aspect, the at least one deformable part comprises a plurality of deformable parts arranged at intervals in a longitudinal direction in the deformable area.

In general, when a shoe contacts with a ground surface during walking, a load path, which represents the shift of a human body weight, occurs on a foot in the forward direction. The load path starts from a lateral side portion of the heel, passes through a lateral side portion of metatarsals, and reaches a medial side portion of the tiptoe. Based on this fact, according to the fifth aspect, the plurality of deformable parts are arranged at intervals in the longitudinal direction. Thus, the planta support surfaces of the plurality of deformable parts can be depressed sequentially in the direction from the heel toward the tiptoe.

A sixth aspect of the present invention is an embodiment of any one of the first to fifth aspects. In the sixth aspect, the base part and the deformable part are arranged adjacent to the medial side of the shoe.

According to the sixth aspect, the base parts and the deformable parts are arranged adjacent to the medial side. This configuration causes the entire foot to be inclined toward the medial side when a patent steps on the ground during walking, and contributes to a decrease in a force (so-called adduction moment) applied to an inside portion of the patient's knee joint in a concentrated manner. Thus, the shoe sole structure according to this aspect can appropriately treat a patient suffering from knee osteoarthritis of the *varus* type (so-called bow legs), and provide the patient with the same or similar effects to those of the first aspect.

A seventh aspect of the present invention is directed to a shoe including the shoe sole structure according to any one of the first to sixth aspects.

According to the seventh aspect, shoes can be provided which are as advantageous as the first to sixth aspects.

Advantages of the Invention

As described above, according to the present invention, in a state where a patient wearing the shoes stands still (a non-moving state), for example, the planta support surface of the deformable part remains substantially flat. On the other hand, when the patient steps forward and his/her shoe contacts with a ground surface, the planta support surface of the deformable part is inclined, causing the entire foot to be inclined toward one of the medial side of the lateral side. This contributes to a decrease in a force applied to an inside or outside portion of the patient's knee joint in a concentrated manner. Thus, the shoe sole structure of the present invention can alleviate symptoms of a patient suffering from knee osteoarthritis, such as pain and swelling of a knee joint that are liable to occur during a movement such as walking, while not allowing the patient to feel his/her plantar surfaces inclined except when the patient is moving, and keeping the patient from developing a habit of walking and standing with his/her plantar surfaces constantly inclined.

DETAILED DESCRIPTION

Embodiments of the present invention will now be described in detail with reference to the drawings. Note that the following description of the embodiments is a mere example in nature, and is not intended to limit the scope, application, or uses of the present invention.

First Embodiment

FIGS. 1 to 4 show a shoe sole structure 1 according to a first embodiment of the present invention. A pair of shoes each including the sole structure 1 and other components, such as a shoe upper, provided for the sole structure 1 may be used as shoes for treating a patient suffering from knee osteoarthritis of a varus type (so-called bow legs). The drawings show the sole structure 1 for a left shoe only. A sole structure 1 for a right shoe is symmetrical to the sole structure 1 for the left shoe. In the following description including the embodiments and variations, only the sole structure 1 for the left shoe will be described and, the description of the sole structure 1 for the right shoe will be omitted. In the following description, the expressions "above," "upward," "on a/the top of," "below," "under," and "downward," represent the vertical positional relationship between respective components of the sole structure 1. The expressions "front," "fore," "forward, "rear," "back," "hind," "behind," and "backward" represent the positional relationship in the longitudinal direction between respective components of the sole structure 1. The expressions "left (side)" "leftward," "right (side)" and "rightward" represent the positional relationship in the width direction between respective components of the sole structure 1.

Figure 2:
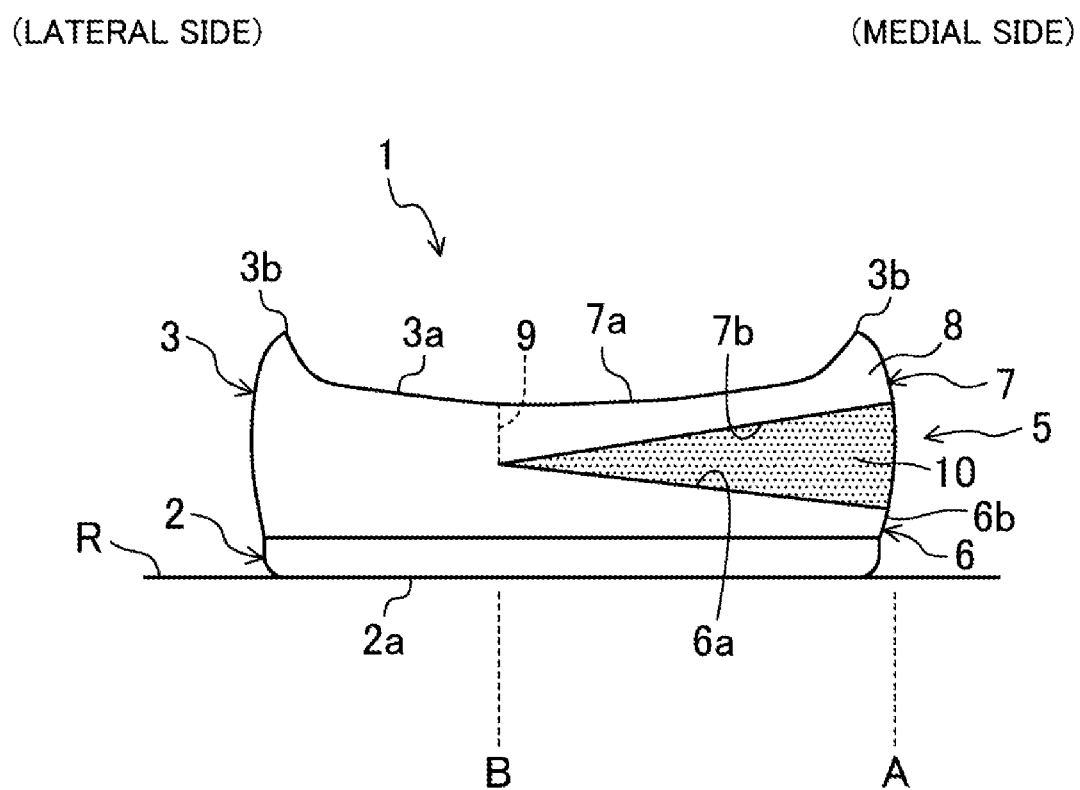
FIG. 2 is a cross-sectional view taken along line II-II in FIG. 1.

As shown in FIG. 2, the sole structure 1 includes an outsole 2 and a midsole 3, as main components. For the sake of convenience, the outsole 2 and the midsole 3 are shown without hatching in FIG. 2.

The outsole 2 extends to correspond to a region, of a human foot, from the tiptoe to a rear side of the heel, and has, on its lower surface, a ground surface 2a configured to contact with a ground surface R. The outsole 2 is made from a hard elastic material which is harder than the material for a midsole 3, which will be described later. Examples of suitable materials for the outsole 2 include thermoplastic resins such as ethylene-vinyl acetate copolymer (EVA), thermosetting resins such as polyurethane (PU), and rubber materials such as butadiene rubber and chloroprene rubber.

Figure 1:
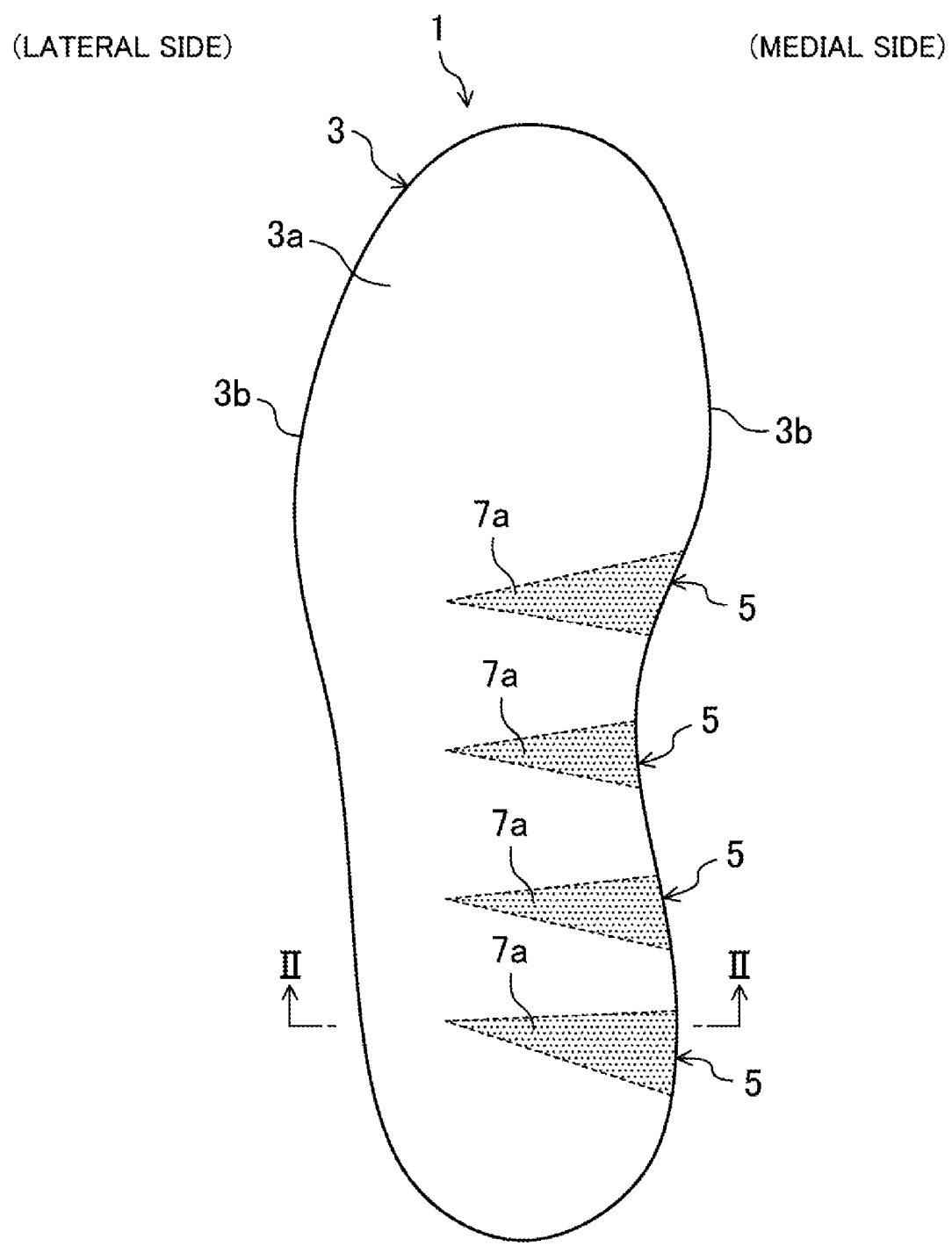
FIG. 1 is a plan view of a shoe sole structure according to a first embodiment of the present invention.

The midsole 3 is configured to support a region, of the plantar surface of a human foot, from the tiptoe to the rear side of the heel. Specifically, as shown in FIGS. 1 and 2, the midsole 3 has, on its upper portion, a planta support surface 3a which is configured to support the plantar surface of the human foot extending from the tiptoe to the rear side of the heel, and which extends in the longitudinal direction. A lower portion of the midsole 3 is bonded to an upper portion of the outsole 2 with an adhesive or the like. Thus, the midsole 3 is stacked on top of the outsole 2. The midsole 3 is made from a soft elastic material. Examples of suitable materials for the midsole 3 include thermoplastic synthetic resins such as ethylene-vinyl acetate copolymer (EVA) and foams of the thermoplastic synthetic resins, thermosetting resins such as polyurethane (PU) and foams of the thermosetting resins, and rubber materials such as butadiene rubber and chloroprene rubber and foams of the rubber materials. A shoe upper (not shown) covering a foot of a patient is attached to a peripheral portion 3b of the midsole 3.

In the sole structure 1, a substantially half portion adjacent to a medial side of the shoe (a right half portion in FIGS. 1 and 2) is configured as a deformable area. The deformable area adjacent to the medial side of the shoe includes deformation allowance portions 5. Each deformation allowance portion 5 is comprised of: a base part 6 which is provided in a medial side portion of the outsole 2 and a medial side lower portion of the midsole 3, the portions being located in the deformable area; a deformable part 7 which is provided in a medial side upper portion of the midsole 3 in the deformable area and which is positioned to correspond to the base part 6 in the vertical direction; and a buffer part 10 provided between the base part 6 and the deformable part 7.

Figure 3:
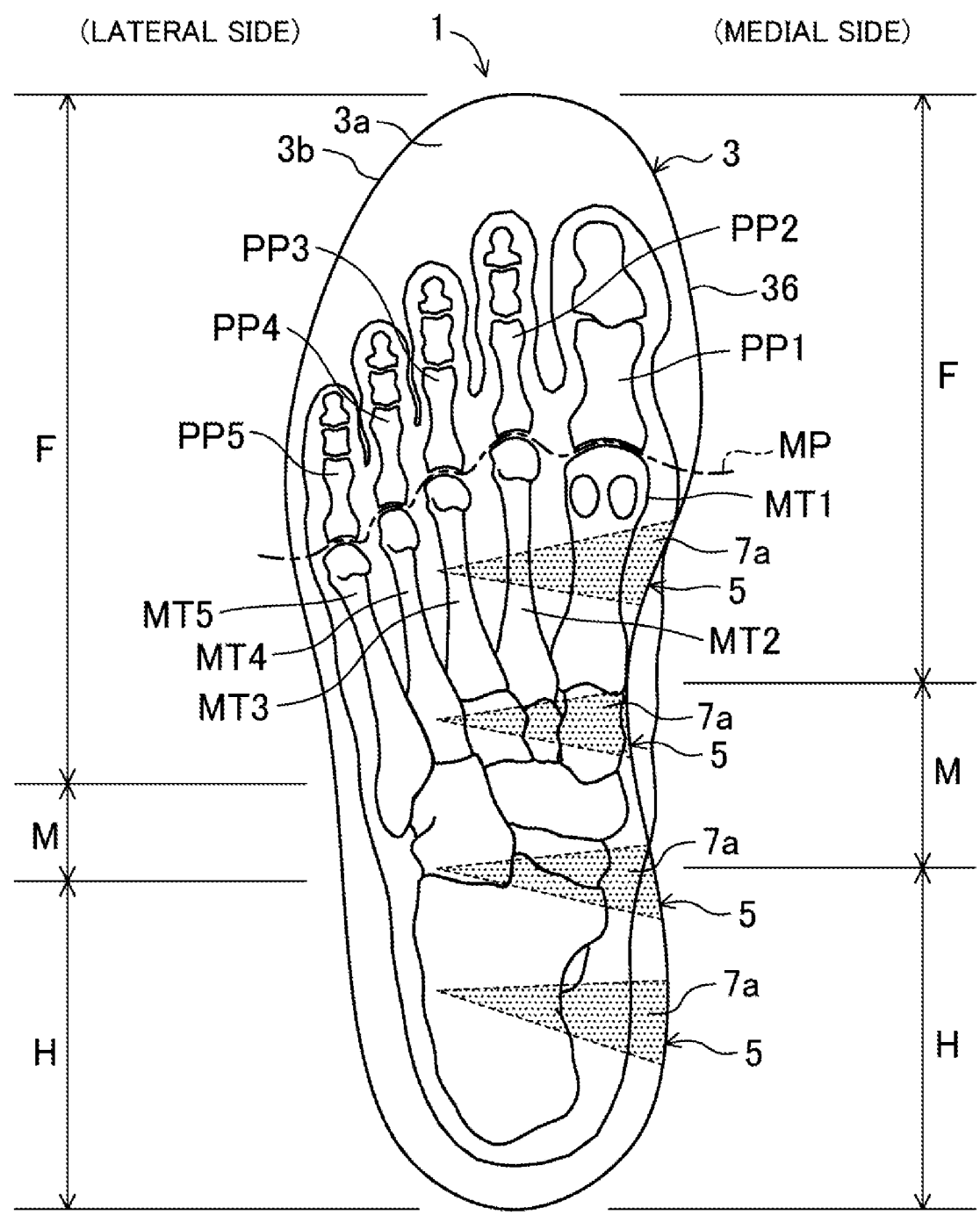
FIG. 3 corresponds to FIG. 1, and shows the sole structure and a skeleton of a human foot in an overlapping fashion.

As shown in FIGS. 1 and 3, the plurality of deformation allowance portions 5 is provided. In plan view, each deformation allowance portion 5 has a tapered shape extending from a medial side portion of the peripheral portion 3b toward a substantially center of the midsole 3 in the width direction. The deformation allowance portions 5, 5, . . . are arranged at intervals in the longitudinal direction.

As shown in FIG. 2, the base part 6 and the deformable part 7 are arranged such that an upper surface 6a of the base part 6 faces a lower surface 7b of the deformable part 7 in the vertical direction, with a predetermined gap interposed therebetween. The gap between the upper surface 6a of the base part 6 and the lower surface 7b of the deformable part 7 narrows continuously and gradually from a distal end side A corresponding to medial side ends of the base part 6 and the deformable part 7 to a base end side B located adjacent to the center in the shoe width direction. More specifically, the upper surface 6a of the base part 6 is inclined upward from the distant end side A corresponding to the medial side end of the base part 6 toward the base end side B, whereas the lower surface 7b of the deformable part 7 is inclined downward from the distal end side A corresponding to the medial side end of the deformable part 7 toward the base end side B. The lower surface 7b of the deformable part 7 meets the upper surface 6a of the base part 6 at a position where a fixed end 9, which will be described later, is formed.

The buffer part 10 is embedded in the midsole 3 between the base part 6 and the deformable part 7. The buffer part 10 is made from a soft elastic material that is softer than the midsole 3. Examples of the materials for the buffer part 10 include thermoplastic synthetic resins such as ethylene-vinyl acetate copolymer (EVA) having a lower hardness than the midsole 3, a foam of ethylene-vinyl acetate copolymer (EVA) having a lower forming rate than the midsole 3, thermosetting resins such as polyurethane having a lower hardness than the midsole 3, and a foam of polyurethane having a lower forming rate than the midsole 3. The buffer part 10 is integrated with, for example, the midsole 3 such that the buffer part 10 is substantially in a wedge shape in cross section.

As shown in FIG. 1, each deformable part 7 has, on its upper surface, a planta support surface 7a configured to support the planta of a human foot. When the shoe is not worn by a patient (see FIG. 2), the planta support surface 7a of the deformable part 7 is flush with a portion, of the planta support surface 3a of the midsole 3, in which the deformation allowance portion 5 is absent. As shown in FIG. 3, the planta support surfaces 7a of the deformable parts 7 are formed to support a region of the plantar surface, of a human, extending from a rear portion of the forefoot F located rearward of the metatarsophalangeal joints MP to the hindfoot H. Note that the metatarsophalangeal joints MP are amphiarthroses which are located between the distal condyles of the metatarsals MT1-MT5 and the proximal condyles of the proximal phalanxes PP1-PP5, and which connect the metatarsals MT1-MT5 to the proximal phalanxes PP1-PP5.

As shown in FIG. 2, the deformable part 7 has a free end 8 adjacent to the distal end side A located on the medial side (at an end in the shoe width direction), and the fixed end 9 located opposite the free end 8, and adjacent to the center in the shoe width direction. The free end 8 is continuous with respective portion of the peripheral portion 3b of the midsole 3 where the deformation allowance portion 5 is absent. The fixed end 9 is located at the position where the upper surface 6a of the base part 6 meets the lower surface 7b of the deformable part 7. As can be seen, the deformable part 7 extends in the width direction (the shoe width direction) from the fixed end 9 located on the base end side B to the free end 8 located on the distal end side A, and functions as an elastic piece of a so-called cantilever structure. Specifically, the deformable part 7 can be flexurally deformed while being supported on the fixed end 9 functioning as a supporting point such that the free end 8 moves downward to come close to the base part 6. In a state where the ground surface 2a of the outsole 2 of the sole structure 1 is in contact with the ground surface R, when one of the planta support surfaces 7a on the upper surface of the deformable parts 7 receives a load of human body caused by walking, the deformable part 7 is flexurally deformed downward while being supported on the respective fixed end 9 functioning as the supporting point. This configuration allows the planta support surface 7a, which is located in the portion where the deformation allowance portion 5 is provided, to be inclined downward such that the free end 8 of the deformable part 7 moves downward, with respect to the planta support surface 3a of the midsole 3.

Next, changes in the deformable part 7 in respective states of use will be described with reference to FIG. 4. The changes constitute a feature of the present invention.

Figure 4:
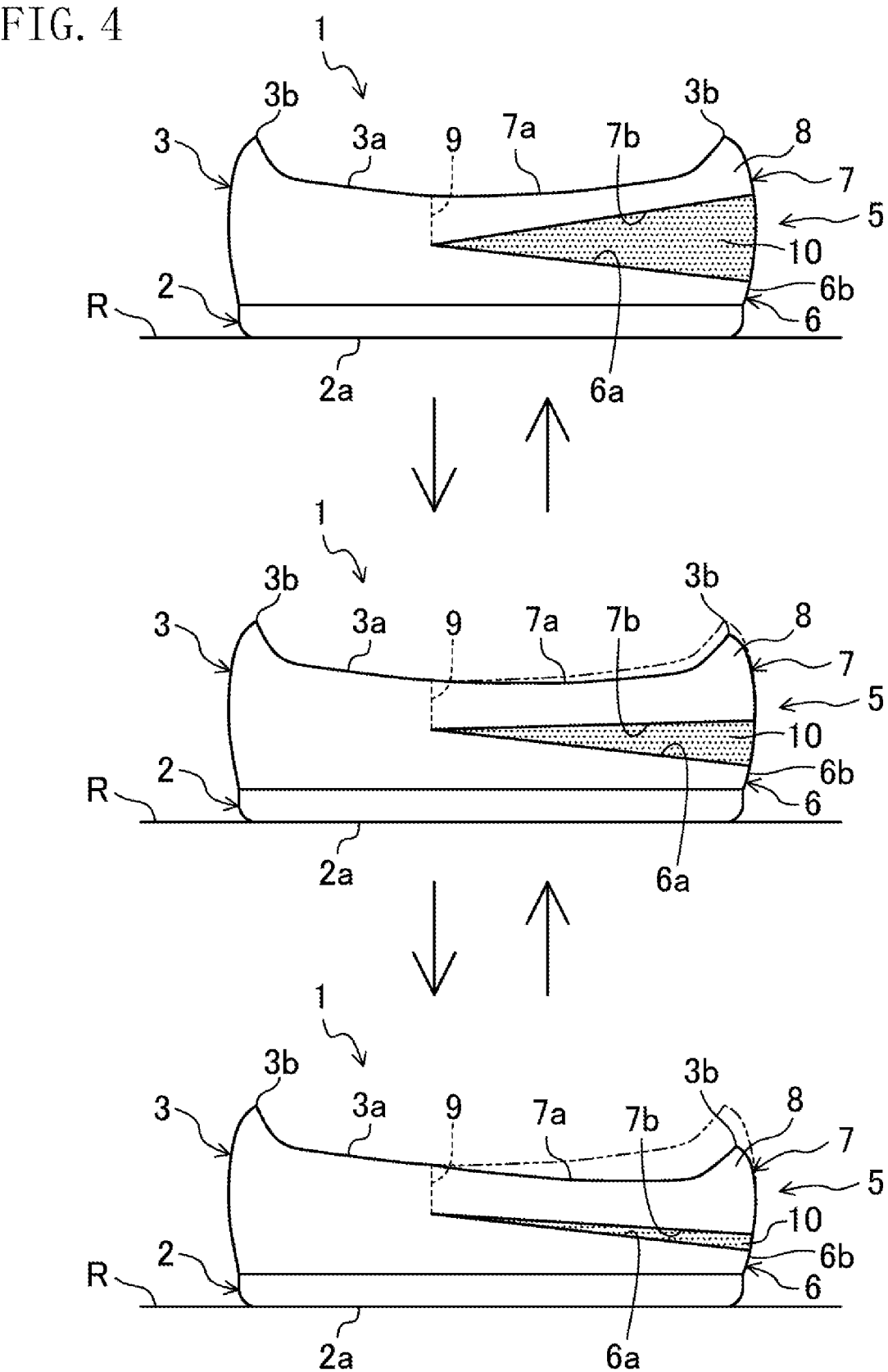
FIG. 4 corresponds to FIG. 2, and shows changes in the sole structure in some states of use.

The upper portion of FIG. 4 shows a state where the shoe is not worn by a patient. In this state, the planta support surface 7a of each deformable part 7 is flush with a portion of the planta support surface 3a of the midsole 3 where the deformation allowance portion 5 is absent, just like the state shown in FIG. 2. In other words, since the load of a human body is not applied to the planta support surface 7a of each deformable part 7 in this state, downward flexural deformation in the deformable part 7 supported on the fixed end 9 does not occur.

The middle portion of FIG. 4 shows a state where the patient wearing the shoes stands still, for example (a non-moving state). In this state, the load of the patient's body is applied evenly to the planta support surface 3a of the entire midsole 3 including the planta support surfaces 7a of the deformable parts 7. As a result, each deformable part 7 is flexurally deformed downward to a slight extent, while being supported on the fixed end 9 functioning as the supporting point. In this state, the planta support surface 7a of each deformable part 7 is slightly inclined downward such that the free end 8 moves downward. In other words, in the state where the patient wearing the shoes stands still, a load not so heavy as the load caused by walking is applied to the deformable parts 7, which are not significantly deformed accordingly. The planta support surfaces 3a and 7a consequently remain substantially flat as a whole. This does not allows the patient to feel inclination of the planta support surfaces 3a and 7a.

Figure 5:
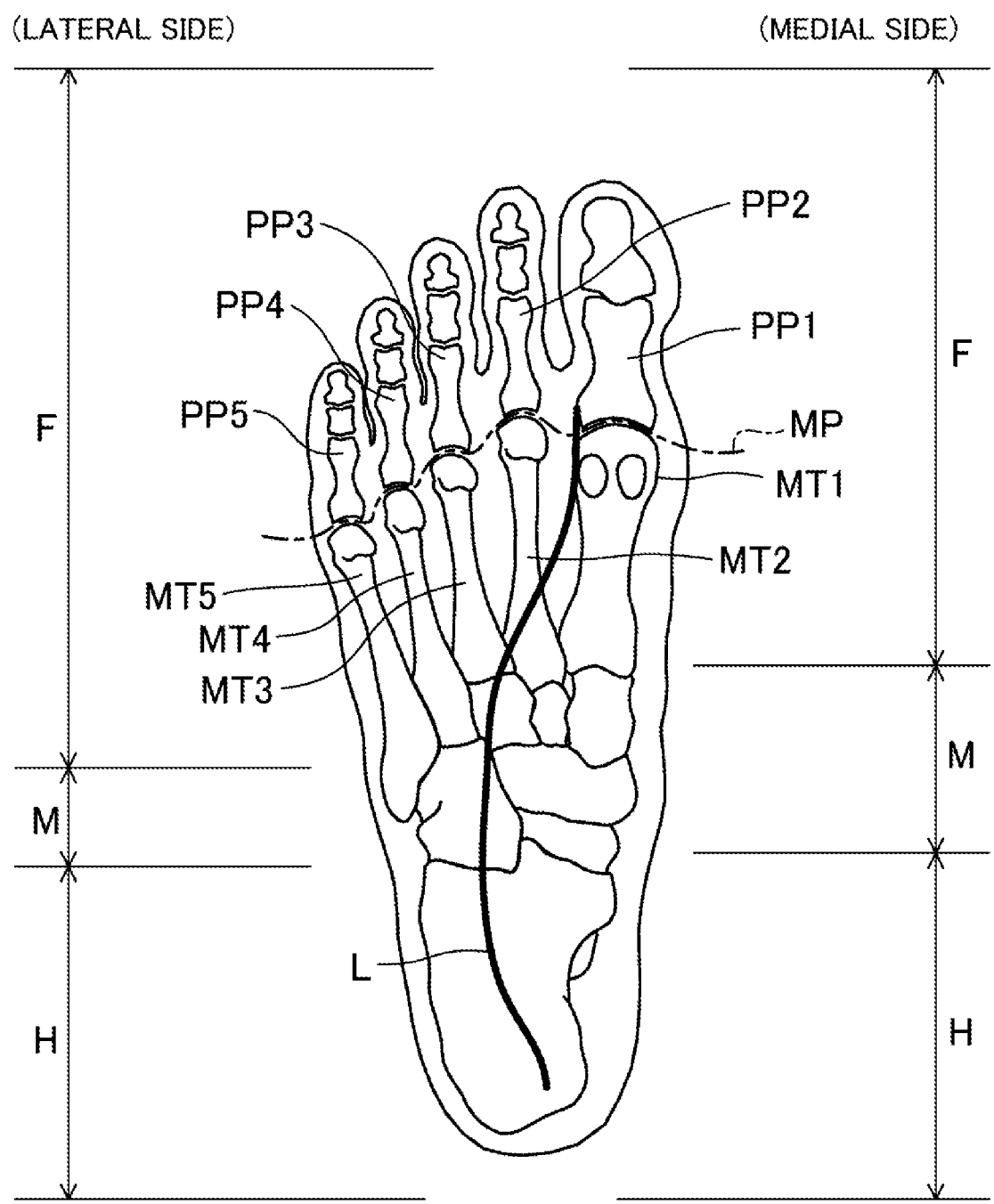
FIG. 5 is a schematic diagram showing a load path on a foot observed when a weight is shifted during walking.

The lower portion of FIG. 4 shows a state where the patient wearing the shoes stepped forward during a movement such as walking and his/her shoe is in contact with the ground surface R. In this state, impact due to the stepping on the ground surface and the load of the patient's body caused by walking are applied to the planta support surfaces 7a of the deformable parts 7. As shown in FIG. 5, in general, a load path L, which represents the shift of the wearer's body weight, occurs on a foot in the forward direction during walking. The load path L starts from a lateral side portion of the heel, passes through a lateral side portion of the metatarsals in the midfoot M, and reaches a medial side portion of the tiptoe. Consequently, when the patient wearing the shoes steps on the ground surface R while walking, impact due to the stepping on the ground surface and the load of the patient's body are locally applied to the planta support surfaces 3a and 7a, in the direction from the heel toward the tiptoe of the foot. Especially in this embodiment, the planta support surfaces 7a of the plurality of deformable parts 7, 7, . . . provided in the area from the rear portion of the forefoot F located rearward of the metatarsophalangeal joints MP to the hindfoot H are depressed sequentially. Specifically, in the state shown in the lower portion of FIG. 4, due to a heavy load applied on the planta support surface 7a, the deformable part 7 becomes flexurally deformed downward while being supported on the fixed end 9 functioning as the supporting point. Consequently, the planta support surface 7a of the deformable part 7 is inclined downward toward the free end 8 more significantly in the state shown in the lower portion of FIG. 4 than in the state shown in the middle portion of FIG. 4. As a result, each foot of the patient who is walking is inclined downward toward the medial side. This can correct the patient's knees each deformed into a shape substantially convex outwardly to the left or right (so-called bow legs) such that the patient's knees come close to each other toward the center, contributing to a decrease in a force applied to the inside portions of the knees of the bow legs (i.e., so-called adduction moment). In this situation, the buffer parts 10 embedded in the midsole 3 are compressed between the upper surface 6a of the base part 6 and the lower surface 7b of the deformable part 7.

During a movement such as walking, when the patient wearing shoes raises his/her foot from the ground surface R to step forward, from the state where the patient has the shoe in contact with the ground surface R (i.e., the state shown in the lower portion of FIG. 4), the shoe sole structure immediately transitions to a state where the load of the patient's body is not applied to the planta support surfaces 7a of the deformable parts 7 (i.e., the state shown in the upper portion of FIG. 4). Also when the patient raises his/her foot from the ground surface R to step forward from the state where the patient stands still (i.e., the state shown in the middle portion of FIG. 4), the shoe sole structure transitions to the state shown in the upper portion of FIG. 4. Once the load of the patient's body is removed from the planta support surface 7a of the deformable part 7, the deformable part 7 moves upward to return to the original position while being supported on the fixed end 9 functioning as the supporting point, so that the planta support surface 7a becomes flush with the planta support surface 3a of the midsole 3.

Advantages of First Embodiment

As can be seen, the shoe sole structure 1 according to this embodiment of the present invention is configured such that in a state where the patient wearing the shoes stands still, for example, (i.e., in a non-moving state), the planta support surface 7a of each deformable part 7 is not significantly inclined toward the medial side and the planta support surfaces 3a and 7a are maintained substantially flush with each other. On the other hand, during a movement such as walking, when the patient wearing the shoes steps forward and the shoe comes into contact with the ground surface R, the load of the patient's body is applied to the planta support surfaces 7a of the deformable parts 7 while the ground surface 2a of the outsole 2 is in contact with the ground surface R. Each deformable part 7 is flexurally deformed downward while supported on the fixed end 9 functioning as the supporting point, and consequently, the planta support surface 7a is inclined downward such that the free end 8 of the deformable part 7 moves downward. Further, in this embodiment, the base parts 6 and the deformable parts 7 are arranged adjacent to the medial side. This configuration causes the entire foot to be inclined toward the medial side in particular when the patent steps on the ground during walking, and contributes to a decrease in the force (the adduction moment) applied to the inside portions of the patient's knee joints in a concentrated manner. Thus, the shoe sole structure 1 according to this embodiment can alleviate symptoms of a patient suffering from knee osteoarthritis of the varus type (so-called bow legs), such as pain and swelling of the knee joints, which are liable to occur during a movement such as walking, while not allowing the patient to feel his/her plantar surfaces inclined except when the patient is moving, and keeping the patient from developing a habit of walking and standing with his/her plantar surfaces constantly inclined.

Moreover, according to this embodiment, the base part 6 and the deformable part 7 are configured such that the gap between the upper surface 6a of the base part 6 and the lower surface 7b of the deformable part 7 narrows in the direction from the distal end side A located at the medial side to the base end side B. Therefore, the free end 8 of the deformable part 7 can make a relatively large movement toward the base part 6. As a result, the planta support surface 7a of the deformable part 7 is easily inclined downward such that the free end 8 moves downward.

The buffer part 10, which is made from an elastic material softer than the midsole 3, is embedded in the midsole 3 between the deformable part 7 and the base part 6. This configuration can substantially prevent abrupt flexural deformation which may occur in the deformable part 7 when the load of a human body is applied to the planta support surface 7a of the deformable part 7, and can impart appropriate cushioning properties to the deformable part 7.

The planta support surfaces 7a of the deformable parts 7 are configured to support a region of the plantar surface extending from a rear portion of the forefoot F located rearward of the metatarsophalangeal joints MP to the hindfoot H, wherein an area of the shoe sole corresponding to this region mainly contacts with the ground surface R during walking. Therefore, the planta support surfaces 7a of the deformable parts 7 can be efficiently inclined toward the medial side, mainly in this region of the plantar surface extending from the rear portion of the forefoot F located rearward of the metatarsophalangeal joints MP to the hindfoot H.

As described earlier, when a patient steps on the ground surface R during walking, the load path L that represents the forward shift of the patient's body weight occurs in general, the load path L starting from a lateral side portion of the heel, passing through a lateral side portion of the metatarsals, and reaching a medial side portion of the tiptoe. Consequently, the load of the patient's body is locally applied to the planta support surfaces 3a and 7a in the direction from the heel to the tiptoe when the patient steps on the ground surface. Based on this fact, this embodiment includes the plurality of deformable parts 7, 7, . . . arranged at intervals in the longitudinal direction. Thus, the planta support surfaces 7a of the plurality of deformable parts 7 are depressed sequentially in the direction from the heel toward the tiptoe.

First Variation of First Embodiment

Figure 6:
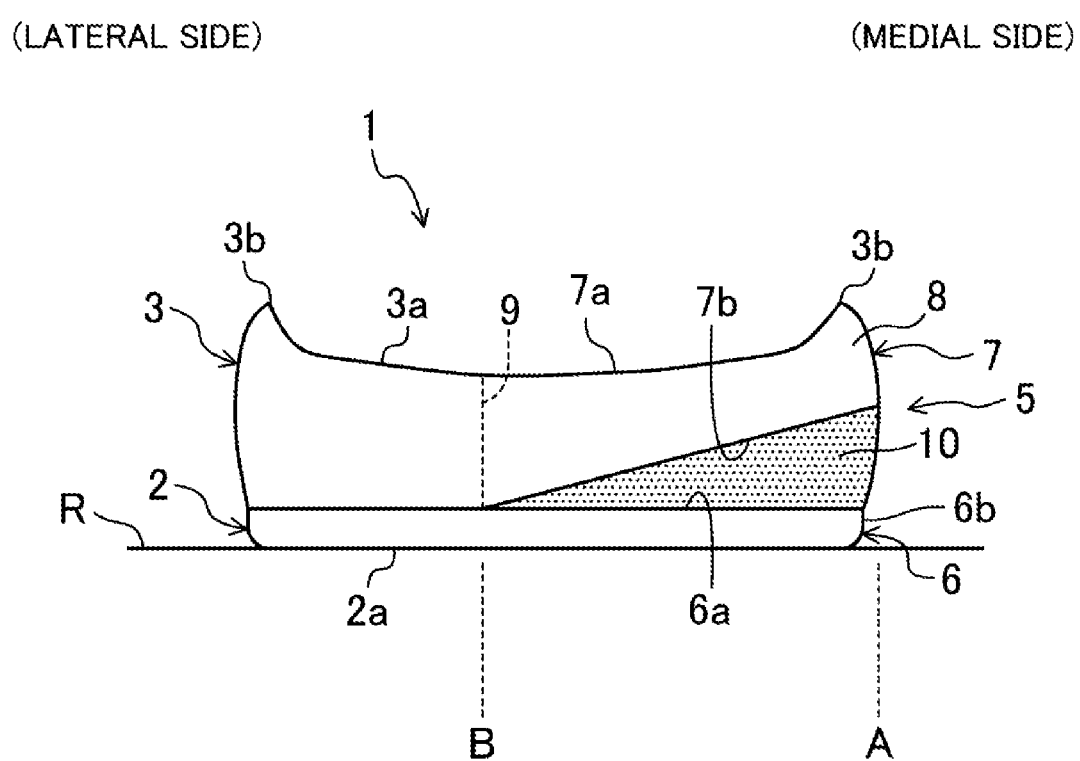
FIG. 6 corresponds to FIG. 2, and shows a first variation of the first embodiment.

FIG. 6 shows a first variation of the first embodiment. Note that the sole structure 1 of each of the following variations is the same as the sole structure 1 of the first embodiment, except differences described below. Therefore, components that are the same as those shown in FIGS. 1 to 5 are denoted by the corresponding reference characters, and a detailed description thereof is omitted herein.

In the sole structure 1 of this variation, the base part 6 is provided in a medial side portion of the outsole 2. That is, the base part 6 does not necessarily have to be provided in a medial side portion of the outsole 2 and a medial side lower portion of the midsole 3. In this variation, the upper surface 6a of the base part 6 corresponds to a medial side portion of the upper surface of the outsole 2, and is substantially horizontal from the distal end side A located on the medial side to the base end side B. The upper surface 6a of the base part 6 meets the lower surface 7b of the deformable part 7 at a position where the fixed end 9 for the deformable part 7 is provided. The buffer part 10 embedded in the midsole 3 between the upper surface 6a of the base part 6 (i.e., the upper surface of the outsole 2) and the lower surface 7b of the deformable part 7 so that the buffer part 10 is substantially in a wedge shape.

Also according to this variation, when the planta support surface 7a of the deformable part 7 receives a load of the body of a patient caused by walking, while a ground surface 2a of the outsole 2 is in contact with the ground surface R, the deformable part 7 can be flexurally deformed downward while being supported on the fixed end 9 functioning as a supporting point, and the planta support surface 7a can be inclined downward such that a free end 8 of the deformable part 7 moves downward.

Second Variations of First Embodiment

Figure 7:
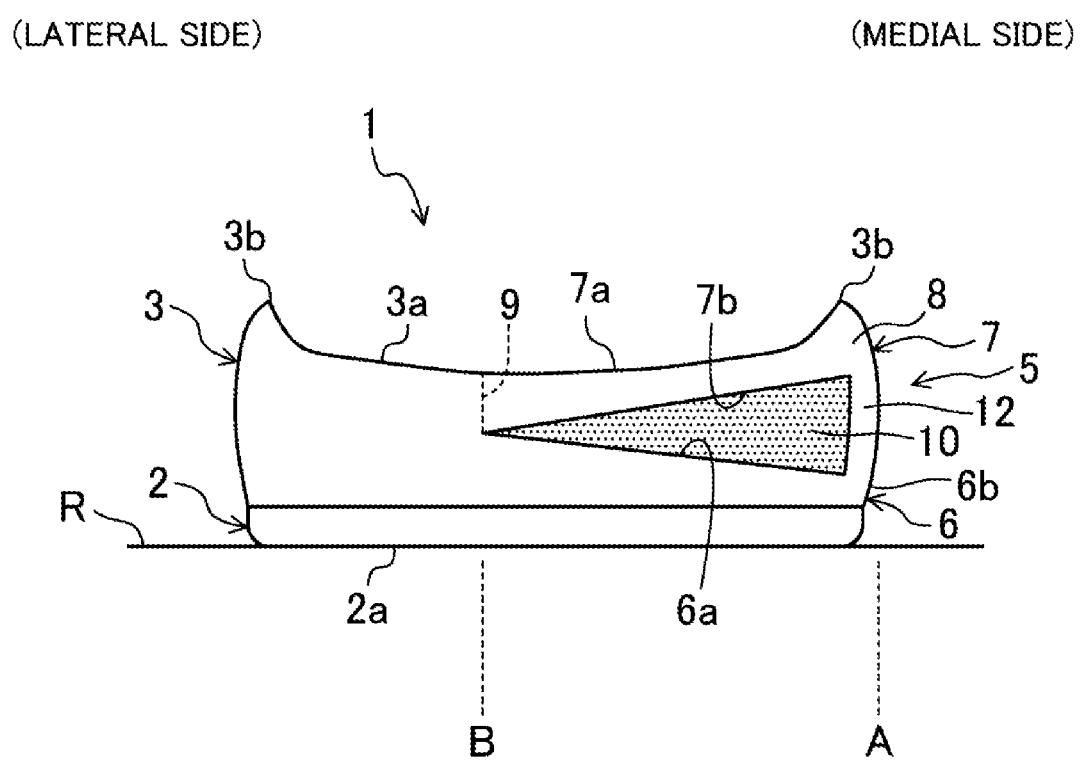
FIG. 7 corresponds to FIG. 2, and shows a second variation of the first embodiment.
Figure 8:
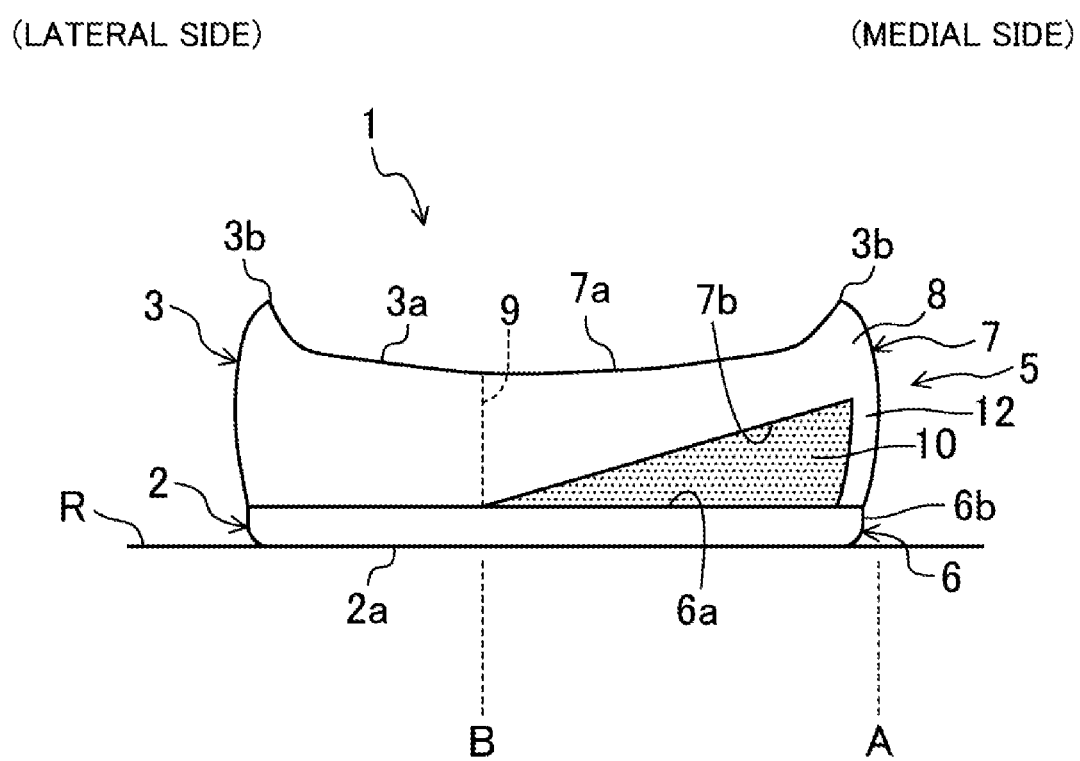
FIG. 8 corresponds to FIG. 2, and shows a further modification of the second variation.

FIGS. 7 and 8 respectively show different second variations of the first embodiment. The sole structure 1 of each of these variations includes a covering part 12 which connects a medial side end 6b of the base part 6 and the free end 8 of the deformable part 7 together in the vertical direction. The covering part 12 is made from the same soft elastic material as that of the midsole 3, and has a small thickness. The covering part 12 covers and conceals a medial side portion of the buffer part 10 and prevents the buffer part 10 from being exposed from a medial side surface to the outside. Also in the variations including the covering part 12, the deformable part 7 is capable of being flexurally deformed while being supported on the fixed end 9 functioning as a supporting point such that the free end 8 moves downward to come close to the base part 6.

Third Variation of First Embodiment

Figure 9:
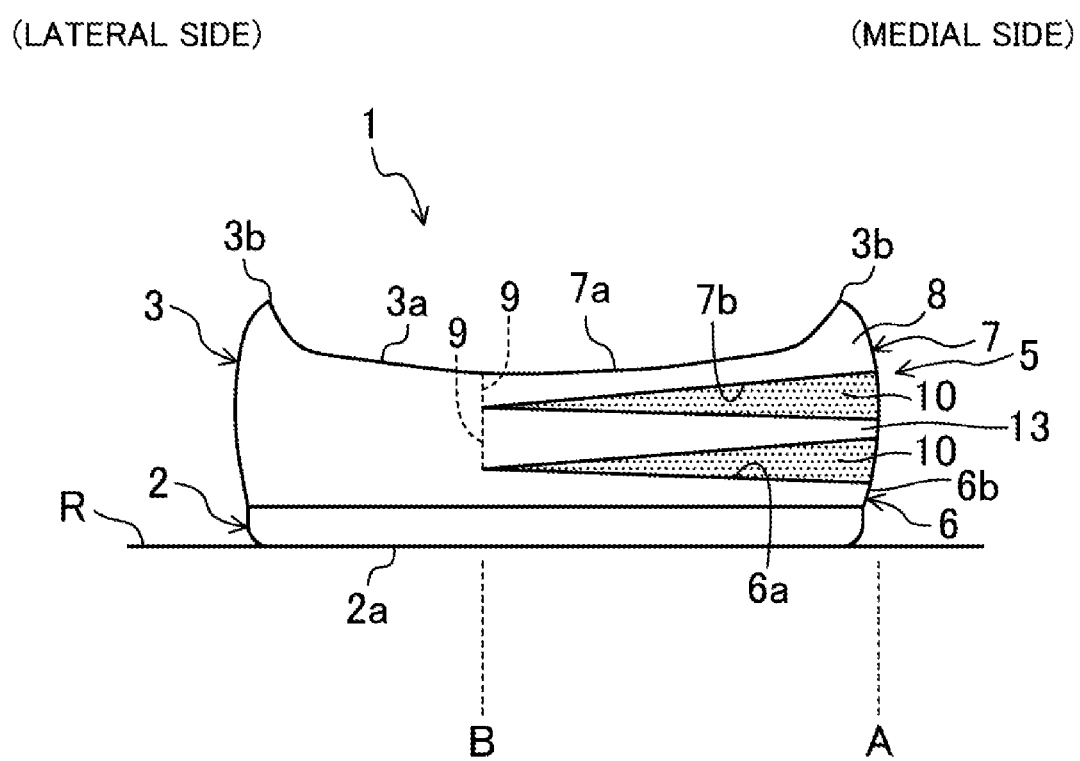
FIG. 9 corresponds to FIG. 2, and shows a third variation of the first embodiment.

FIG. 9 shows a third variation of the first embodiment. The sole structure 1 of this variation includes an intermediate part 13 comprised of a portion of the midsole 3 and provided between the base part 6 and the deformable part 7. Buffer parts 10, 10 are each embedded in the midsole 3 between the deformable part 7 and the intermediate part 13 and between the intermediate part 13 and the base part 6. Similarly to the deformable part 7, the intermediate part 13 also extends from the fixed end 9 adjacent to the base end side B to the free end 8 adjacent to the distal end side A in the width direction. Thus, the intermediate part 13 functions as an elastic piece of a so-called cantilever structure. The intermediate part 13 can be flexurally deformed while being supported on the fixed end 9 such that the free end 8 moves downward to come close to the base part 6.

Thus, in this variation, when the planta support surface 7a of the deformable part 7 receives a load of the body of a patient, while a ground surface 2a of the outsole 2 is in contact with the ground surface R, the deformable part 7 and the intermediate part 13 can be flexurally deformed downward while being supported on the respective fixed ends 9 functions as supporting points, and the planta support surface 7a can be inclined downward such that the free end 8 of the deformable part 7 moves downward.

Fourth Variation of First Embodiment

Figure 10:
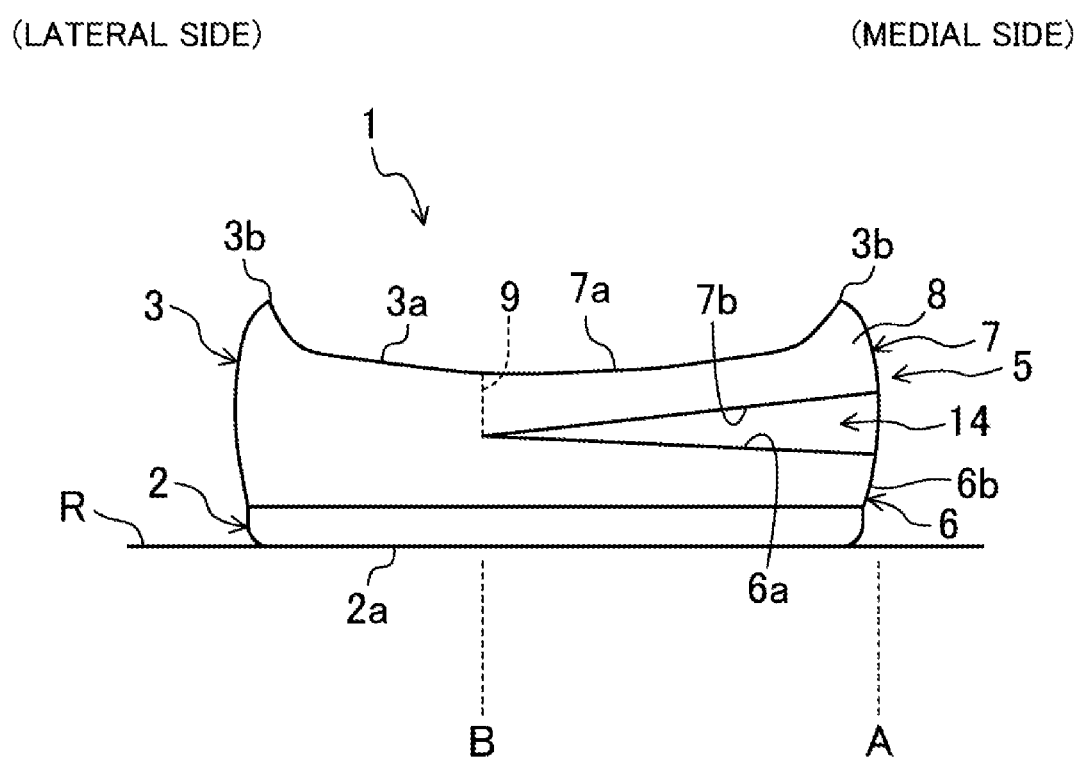
FIG. 10 corresponds to FIG. 2, and shows a fourth variation of the first embodiment.

FIG. 10 shows a fourth variation of the first embodiment. The sole structure 1 of this variation does not include the buffer part 10 of the first embodiment, but includes a notch 14 which is a hollow space having a substantially wedge shape and which is provided between the upper surface 6a of the base part 6 and the lower surface 7b of the deformable part 7. That is, the deformation allowance portion 5 does not necessarily have to include the buffer part 10. Also according to this variation, when the planta support surface 7a of the deformable part 7 receives a load of the body of a patient, while a ground surface 2a of the outsole 2 is in contact with the ground surface R, the deformable part 7 can be flexurally deformed downward while being supported on the fixed end 9 functioning as a supporting point, and the planta support surface 7a can be inclined downward such that a free end 8 of the deformable part 7 moves downward.

Fifth Variation of First Embodiment

Figure 11:
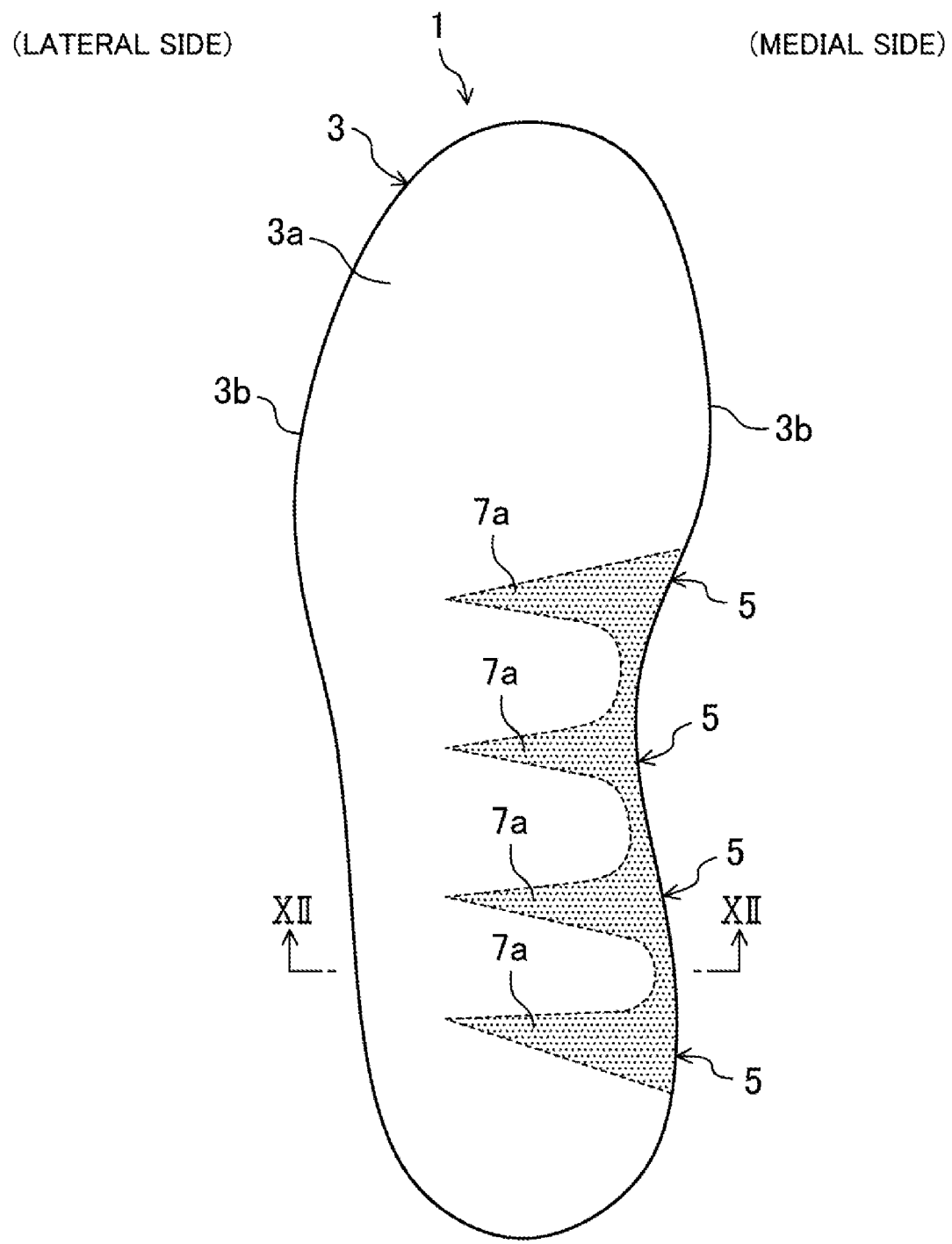
FIG. 11 corresponds to FIG. 1, and shows a fifth variation of the first embodiment.
Figure 12:
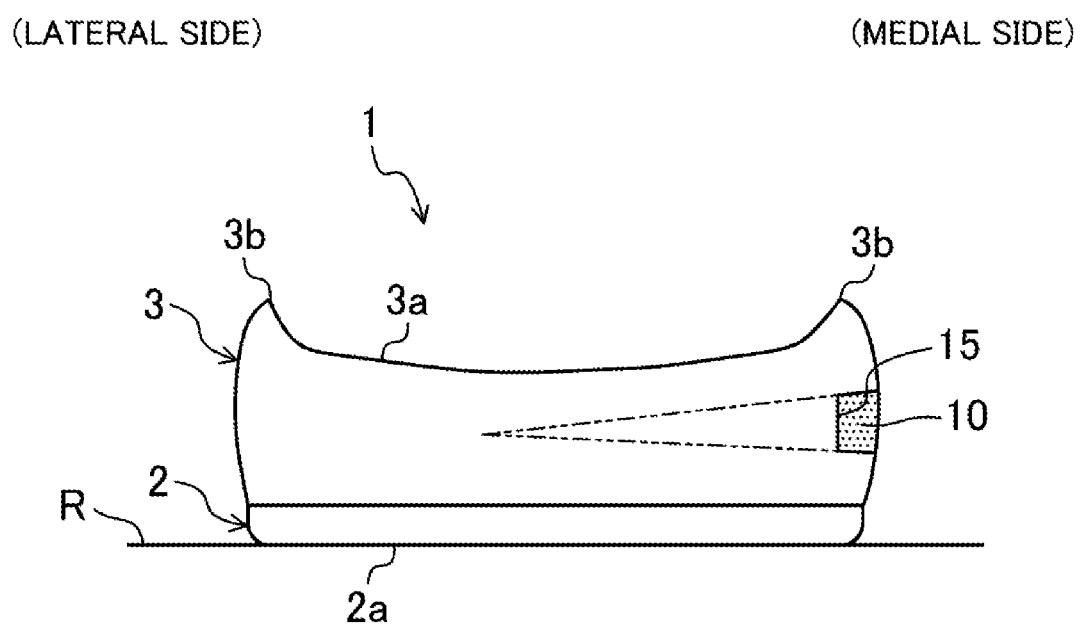
FIG. 12 is a cross-sectional view taken along line XII-XII in FIG. 11.

FIG. 11 shows a fifth variation of the first embodiment. The sole structure 1 of this variation includes a plurality of deformation allowance portions 5, 5, . . . which are arranged at intervals in the longitudinal direction, and which are continuous and integral with one another on a peripheral portion 3b adjacent to the medial side portion of a midsole 3. That is, the deformation allowance portions 5 do not necessarily have to be completely independent from one anther in the longitudinal direction. Specifically, as shown in FIG. 12, on the side surface of the peripheral portion 3b adjacent to the medial side of the midsole 3, a recess 15 which is a recessed notch is formed between longitudinally adjacent ones of the deformation allowance portions 5, 5. Each recess 15 has a buffer part 10 embedded therein. The buffer parts 10 are continuous with each other between the longitudinally adjacent ones of the deformation allowance portions 5.

Sixth Variation of First Embodiment

Figure 13:
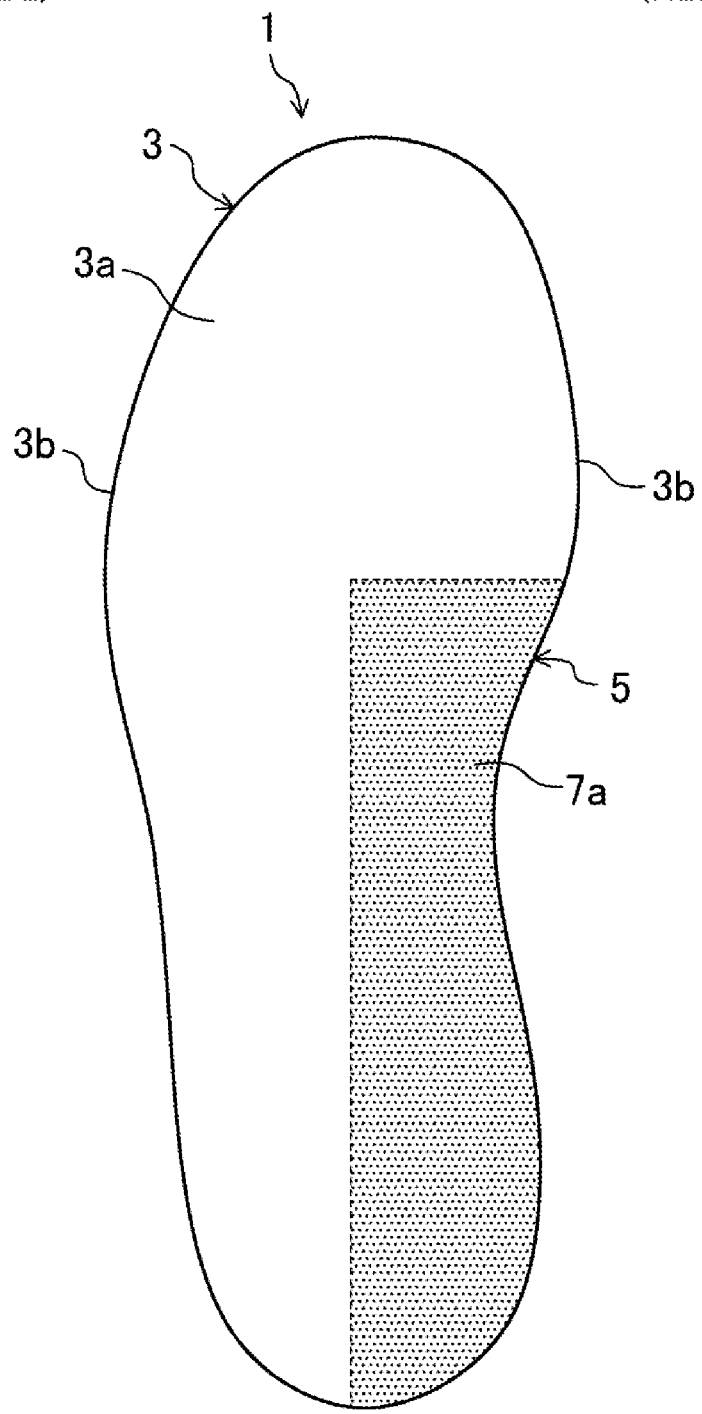
FIG. 13 corresponds to FIG. 1, and shows a sixth variation of the first embodiment.

FIG. 13 shows a sixth variation of the first embodiment. The sole structure 1 of this variation includes a single deformation allowance portion 5 that extends to correspond to a region from a rear portion of the forefoot F located rearward of the metatarsophalangeal joints MP to the hindfoot H. That is, it is not essential that the plurality of deformation allowance portions 5 are arranged independently from one another in the longitudinal direction.

Second Embodiment

Figure 14:
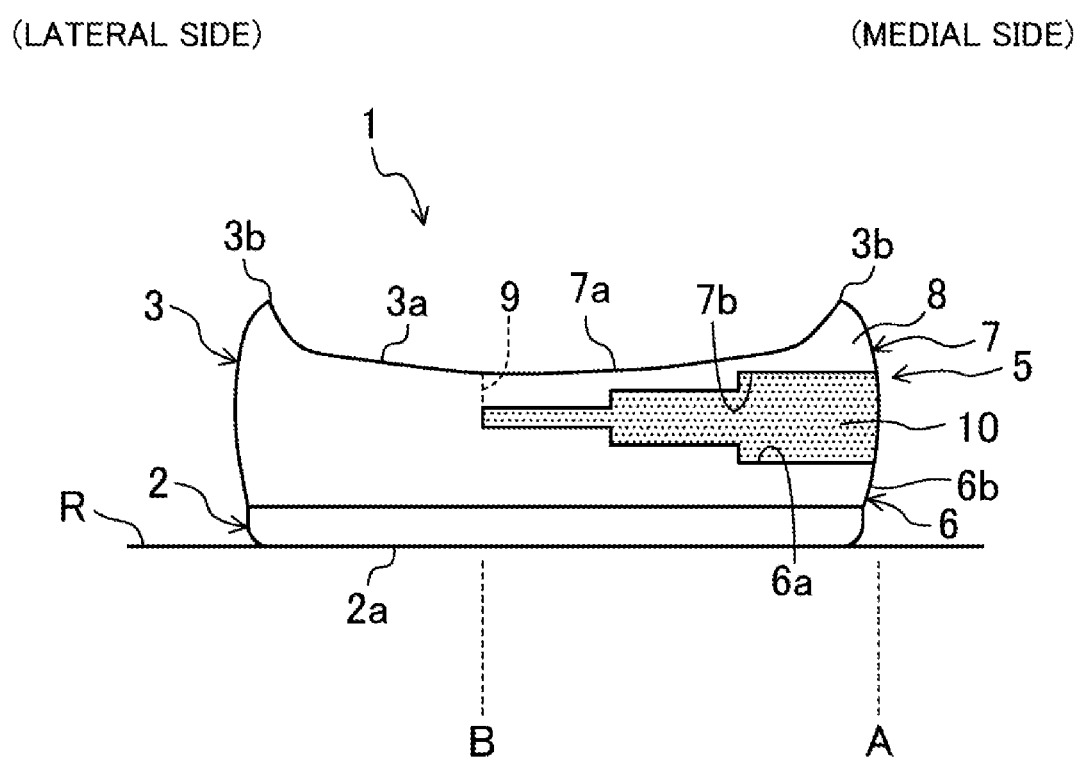
FIG. 14 corresponds to FIG. 2, and shows a sole structure according to a second embodiment.
Figure 15:
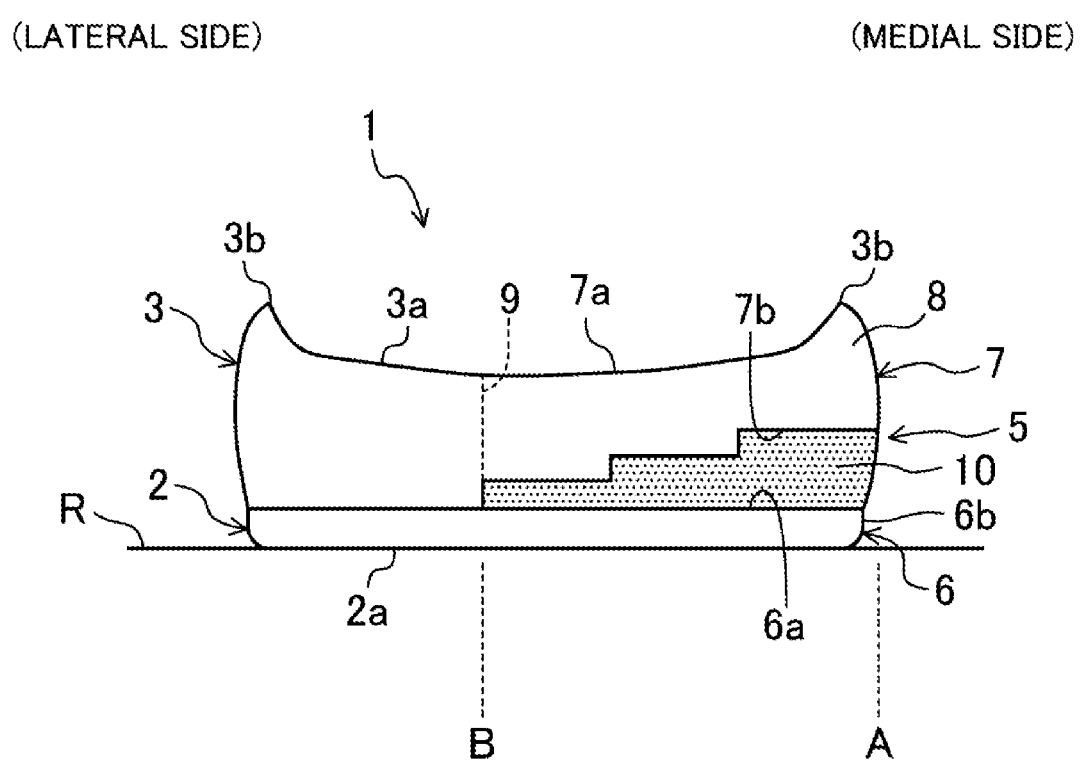
FIG. 15 corresponds to FIG. 1, and shows a first variation of the second embodiment.

FIGS. 14 and 15 show a sole structure 1 according to a second embodiment of the present invention. The second embodiment differs from the first embodiment in the shapes of the base part 6 and the deformable part 7. Note that the sole structure 1 of this embodiment is the same as the sole structure 1 of the first embodiment, except these differences. Therefore, components that are the same as those shown in FIGS. 1 to 13 are denoted by the corresponding reference characters, and a detailed description thereof is omitted herein.

As shown in FIG. 14, the base part 6 and the deformable part 7 are shaped such that the gap between the upper surface 6a of the base part 6 and the lower surface 7b of the deformable part 7 narrows in a stepwise manner in the direction from the distal end side A located at the medial side to the base end side B. Specifically, the upper surface 6a of the base part 6 has steps such that the thickness of the base part 6 in the vertical direction increases in a stepwise manner in the direction from the distal end side A located at the medial side to the base end side B. Similarly, the lower surface 7b of the deformable part 7 has steps such that the thickness of the deformable part 7 in the vertical direction increases in a stepwise manner in the direction from the free end 8 adjacent to the distal end side A to the fixed end 9 adjacent to the base end side B.

As can be seen, the base part 6 and the deformable part 7 do not necessarily have to be configured such that the gap between the upper surface 6a of the base part 6 and the lower surface 7b of the deformable part 7 narrows continuously and gradually in the direction from the distal end side A located at the medial side to the base end side B. The base part 6 and the deformable part 7 may be configured such that the gap therebetween narrows in a stepwise manner.

FIG. 15 shows a variation of the second embodiment. This variation corresponds to the first variation of the first embodiment, and a detailed description of this variation will be omitted herein. Although the second embodiment includes variations corresponding to the second to sixth variations of the first embodiment, detailed description of the variations of the second embodiment is omitted to avoid overlapping.

Third Embodiment

Figure 16:
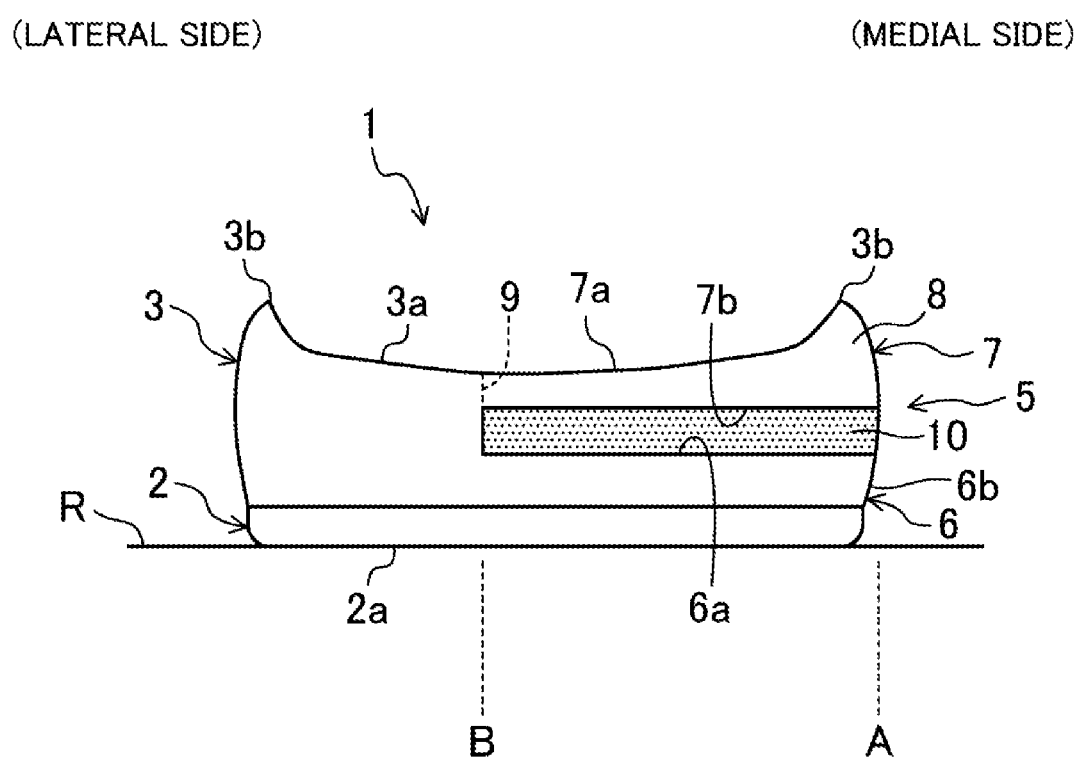
FIG. 16 corresponds to FIG. 2, and shows a sole structure according to a third embodiment.
Figure 17:
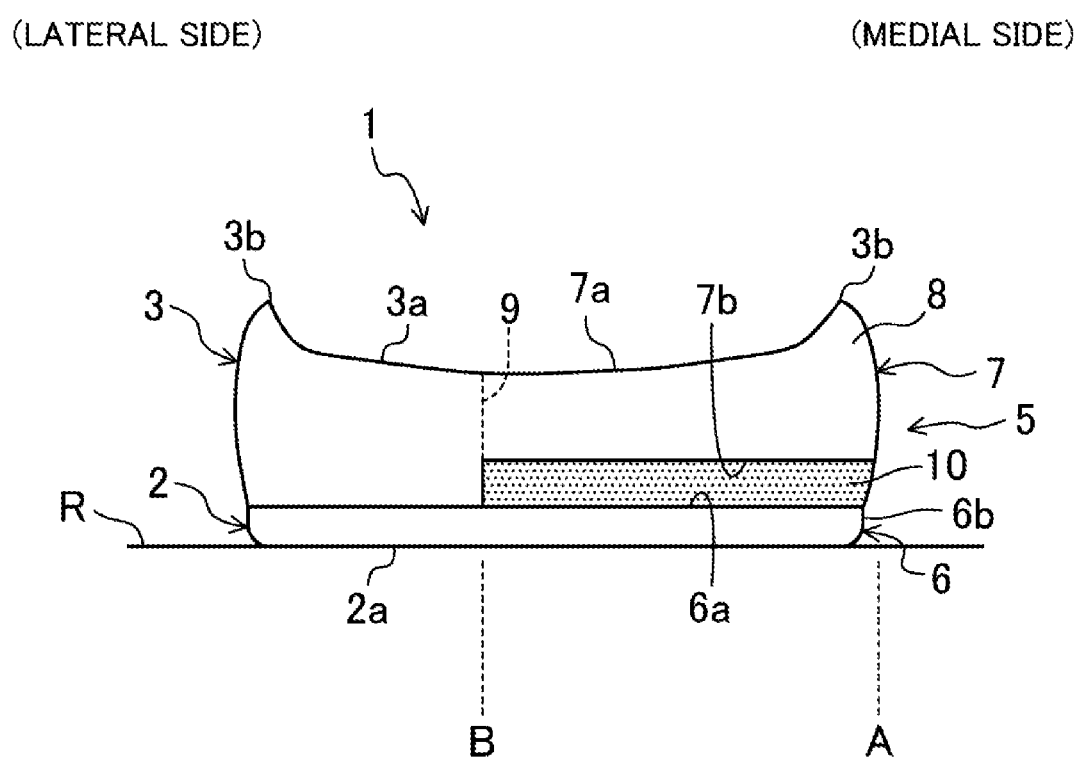
FIG. 17 corresponds to FIG. 6, and shows a first variation of the third embodiment.

FIGS. 16 and 17 show different sole structures 1 according to a third embodiment of the present invention. The third embodiment also differs from the first embodiment in the shapes of the base part 6 and the deformable part 7. Note that the sole structure 1 of this embodiment is the same as the sole structure 1 of the first embodiment, except these differences. Therefore, components that are the same as those shown in FIGS. 1 to 13 are denoted by the corresponding reference characters, and a detailed description thereof is omitted herein.

In the example shown in FIG. 16, the base part 6 and the deformable part 7 are shaped such that the gap between the upper surface 6a of the base part 6 and the lower surface 7b of the deformable part 7 is constant in the direction from the distal end side A located at the medial side to the base end side B. Specifically, the upper surface 6a of the base part 6 and the lower surface 7b of the deformable part 7 extend substantially horizontally from the distal end side A located at the medial side toward the base end side B. A buffer part 10 is embedded in the midsole 3 between the base part 6 and the deformable part 7 such that the buffer part 10 has a substantially rectangular shape in cross section.

As can be seen, the base part 6 and the deformable part 7 do not necessarily have to be configured such that the gap between the upper surface 6a of the base part 6 and the lower surface 7b of the deformable part 7 narrows in the direction from the distal end side A located at the medial side to the base end side B. The base part 6 and the deformable part 7 may be configured such that the gap therebetween is constant.

FIG. 17 shows a variation of the third embodiment. This variation corresponds to the first variation of the first embodiment, and therefore, a detailed description of this embodiment will be omitted herein. Although the third embodiment includes variations corresponding to the second to sixth variations of the first embodiment, detailed description of the variations of the second embodiment is omitted to avoid overlapping.

Other Embodiments

In the first embodiment, the first to sixth variations are each described. However, two or more of these variations may be combined with each other as appropriate. The same applies to the second and third embodiments.

The sole structure 1 of each of the embodiments described above includes the base parts 6 and the deformable parts 7 that are provided adjacent to the medial side. However, this is merely a non-limiting example. Specifically, the base parts 6 and the deformable parts 7 may be provided adjacent to the lateral side. With such an embodiment in which the base parts 6 and the deformable parts 7 are arranged adjacent to the lateral side, a foot of a patient is inclined toward the lateral side when the patient steps on the ground surface during walking. This contributes to a decrease in a force applied to outside portions of the patient's knees in a concentrated manner. Thus, according to this embodiment, a patient suffering from knee osteoarthritis of the valgus type (so-called knock knees) can be treated appropriately such that the same or similar effects to the first embodiment can be obtained.

In the sole structure 1 of each of the embodiments described above, the planta support surfaces 7a of the deformable parts 7 are formed to support a region of the plantar surface extending from a rear portion of the forefoot F located rearward of the metatarsophalangeal joints MP to the hindfoot H. However, this is merely a non-limiting example. Specifically, the planta support surfaces 7a of the deformable parts 7 may support the entire plantar surface including the forefoot F, the midfoot M, and the hindfoot H.

Note that the present invention is not limited to the embodiments described above, and various changes and modifications may be made without departing from the scope of the present invention.

INDUSTRIAL APPLICABILITY

The present invention is industrially usable as a shoe sole structure and shoes including the shoe sole structure that are usable for a patient suffering from knee osteoarthritis.

DESCRIPTION OF REFERENCE CHARACTERS

1 Sole Structure
2 Outsole
3 Midsole
3a Planta Support Surface
5 Deformation Allowance Portion
6 Base Part
7 Deformable Part
7a Planta Support Surface
8 Free End
9 Fixed End
10 Buffer Part
12 Covering Part
13 Intermediate Part
14 Notch
15 Recess
MP Metatarsophalangeal Joints
F Forefoot
H Hindfoot
L Load Path
A Distal End Side
B Base End Side
R Ground Surface

The invention claimed is:

1. A shoe sole structure including an outsole having a ground contact surface configured to contact with a ground surface, a midsole made from an elastic material and stacked on an upper portion of the outsole, and a deformable area provided in a medial side portion or a lateral side portion, the deformable area having at least one deformation allowance portion adapted to be arranged at a position corresponding to a region of a foot of a human body that extends from a rear portion of a forefoot located rearward of metatarsophalangeal joints to a hindfoot, the at least one deformation allowance portion including:

at least one base part provided in a portion of the outsole, or a portion of the outsole and a lower portion of the midsole, the portions being located in the deformable area; and at least one deformable part provided in an upper portion of the midsole, the upper portion being located in the deformable area, the at least one deformable part corresponding to the at least one base part in a vertical direction, having a lower surface which faces an upper surface of the at least one base part with a gap interposed between the lower and upper surfaces, including, on an upper surface thereof, a planta support surface which is configured to support a planta of a human body, and being flexurally deformable while being supported on a fixed end on a base end side adjacent to a center in a shoe width direction such that a free end on a distal end side adjacent to an end in the shoe width direction moves downward to come close to the at least one base part, wherein a buffer part made from a soft elastic material which is softer than the midsole is embedded in the midsole between the deformable part and the base part, the lower surface of the deformable part inclines downward from the distal end side to the base end side in a cross section, and in a state where the ground contact surface of the outsole is in contact with the ground surface, when the planta support surface on the upper surface of the at least one deformable part receives a load of the human body caused by walking, the at least one deformable part is flexurally deformed downward while being supported on the fixed end functioning as a supporting point, thereby allowing the planta support surface to be inclined downward such that the free end of the deformable part moves downward.

2. The sole structure of claim 1, wherein
the gap between the lower surface of the deformable part and the upper surface of the base part narrows in a direction from a distal end side to the base end side of the deformable part.

3. A shoe comprising the shoe sole structure of claim 2.

4. The shoe sole structure of claim 1, wherein
the at least one deformable part comprises a plurality of deformable parts arranged at intervals in a longitudinal direction in the deformable area.

5. A shoe comprising the shoe sole structure of claim 4.

6. The shoe sole structure of claim 1, wherein
the base part and the deformable part are arranged adjacent to the medial side of the shoe.

7. A shoe comprising the shoe sole structure of claim 6.

8. A shoe comprising the shoe sole structure of claim 1.

* * * * *